(12) United States Patent
Schmidgall et al.

(10) Patent No.: US 8,474,325 B1
(45) Date of Patent: Jul. 2, 2013

(54) APPARATUS AND METHOD FOR DESTRUCTIVE LOAD TESTING

(75) Inventors: Ronald D. Schmidgall, Burlington, IA (US); Darren C. Delzell, Burlington, IA (US); David E. Stoller, Burlington, IA (US)

(73) Assignee: Hawkeye Concrete Products Co., Mediapolis, IA (US)

( * ) Notice: Subject to any disclaimer, the term of this patent is extended or adjusted under 35 U.S.C. 154(b) by 383 days.

(21) Appl. No.: 12/861,216

(22) Filed: Aug. 23, 2010

(51) Int. Cl.
*G01N 3/08* (2006.01)

(52) U.S. Cl.
USPC .............. 73/821; 73/760; 73/788; 73/818

(58) Field of Classification Search
USPC .............. 73/784, 788, 803, 818, 821; 72/199, 72/210; 83/401, 451, 730; 108/52.1, 57.13
See application file for complete search history.

(56) References Cited

U.S. PATENT DOCUMENTS 5,030,055 A * 7/1991 Parks et al. ............ 414/282
6,301,956 B1 * 10/2001 Fujita et al. ............... 73/82

* cited by examiner

*Primary Examiner* — Harshad R Patel
*Assistant Examiner* — Roger Hernandez-Prewitt
(74) *Attorney, Agent, or Firm* — Jason R. Sytsma; Shuttleworth & Ingersoll, PLC

(57) ABSTRACT

According to the present invention, there is provided an apparatus for positioning a specimen to be tested relative to an external force applicator. The external force applicator is adapted for engaging the specimen for test purposes. A defined path extends between a first position away from the external load applicator and a second position underneath the external load applicator. A carriage positioned on the defined path moves relative to the external force applicator between the first position which is a loading position away from the external force applicator and the second position which is an engagement position. When the specimen is in the second engagement position, the external force applicator can engage the specimen to conduct the test.

27 Claims, 10 Drawing Sheets

APPARATUS AND METHOD FOR DESTRUCTIVE LOAD TESTING

FIELD

The present invention relates to an apparatus for destructively testing a specimen, and more specifically to an apparatus and method for positioning the specimen for destructive testing.

BACKGROUND

Manufactures of concrete pipe, tile, man hole sections, and the like are required by ASTM International (ASTM) to perform a number of tests on their products to insure the products meet the stringent safety and reliability demands of the ASTM standards. One of these tests is the "External Load Crushing Test by the Three-Edge Bearing Test Method," found in ASTM C 497 (the "Crush Test").

The Crush Test applies an external load to the specimen and measures the point at which it cracks. A specimen is supported on a pair of lower bearings and a load is applied through an upper bearing. The prior art is replete with machines designed specifically for the Crush Test. Most of which require the specimen to be placed on a support frame then manually cajoled into position on top of the lower bearing and underneath the upper bearing. The task is arduous and time consuming.

SUMMARY

According to the present invention, there is provided an apparatus for positioning a specimen to be tested relative to an external force applicator. The external force applicator is adapted for engaging the specimen for test purposes. A defined path extends between a first position away from the external load applicator and a second position underneath the external load applicator. A carriage positioned on the defined path moves relative to the external force applicator between the first position which is a loading position away from the external force applicator and the second position which is an engagement position. When the specimen is in the second engagement position, the external force applicator can engage the specimen to conduct the test.

The carriage is provided with at least two rollers on opposite lateral sides of the carriage for selectively supporting the carriage for movement along the path. The rollers are moveable between a first position wherein the carriage is supported above the path for movement along the path and a second position wherein the carriage is contiguous with a lower load beam in the path such that the external force applicator can engage the specimen and the carriage remains stationary.

The carriage also includes a pair of parallel bearings rectangular in cross section positioned laterally across the carriage. A first and a second moveable support adapted for synchronized longitudinal inward and outward movement with respect to the center of the carriage lowers the specimen on to the bearings. In an embodiment, centering rollers rotationally support the specimen so that the specimen is moveable to a center position with its center of gravity between the pair of parallel bearings before it is lowered on to the bearings by the outward movement of the moveable support.

In another embodiment, there is provided a method for destructive testing of a specimen. A specimen is positioned on a carriage, which carriage has rollers and a pair of bearing strips. The specimen is then rotated until a vertical plane bisecting the specimen is normal to a top surface of the bearing strips. The specimen is then lowered on to the bearing strips such that the load is substantially equally dispersed upon both of the bearing strips. Next, the carriage is moved to a position such that the vertical plane bisecting the specimen is in alignment with an upper bearing on an external force applicator. The carriage is lowered on to a rigid structure. Finally downward external force is applied to the specimen, in order to carry out the destructive test.

Other aspects, features, and embodiments of the invention will become apparent upon review of the following description taken in connection with the accompanying drawings. The invention, though, is pointed out with particularity by the appended claims.

BRIEF DESCRIPTION OF THE ILLUSTRATED EMBODIMENTS

DETAILED DESCRIPTION

Figure 1:
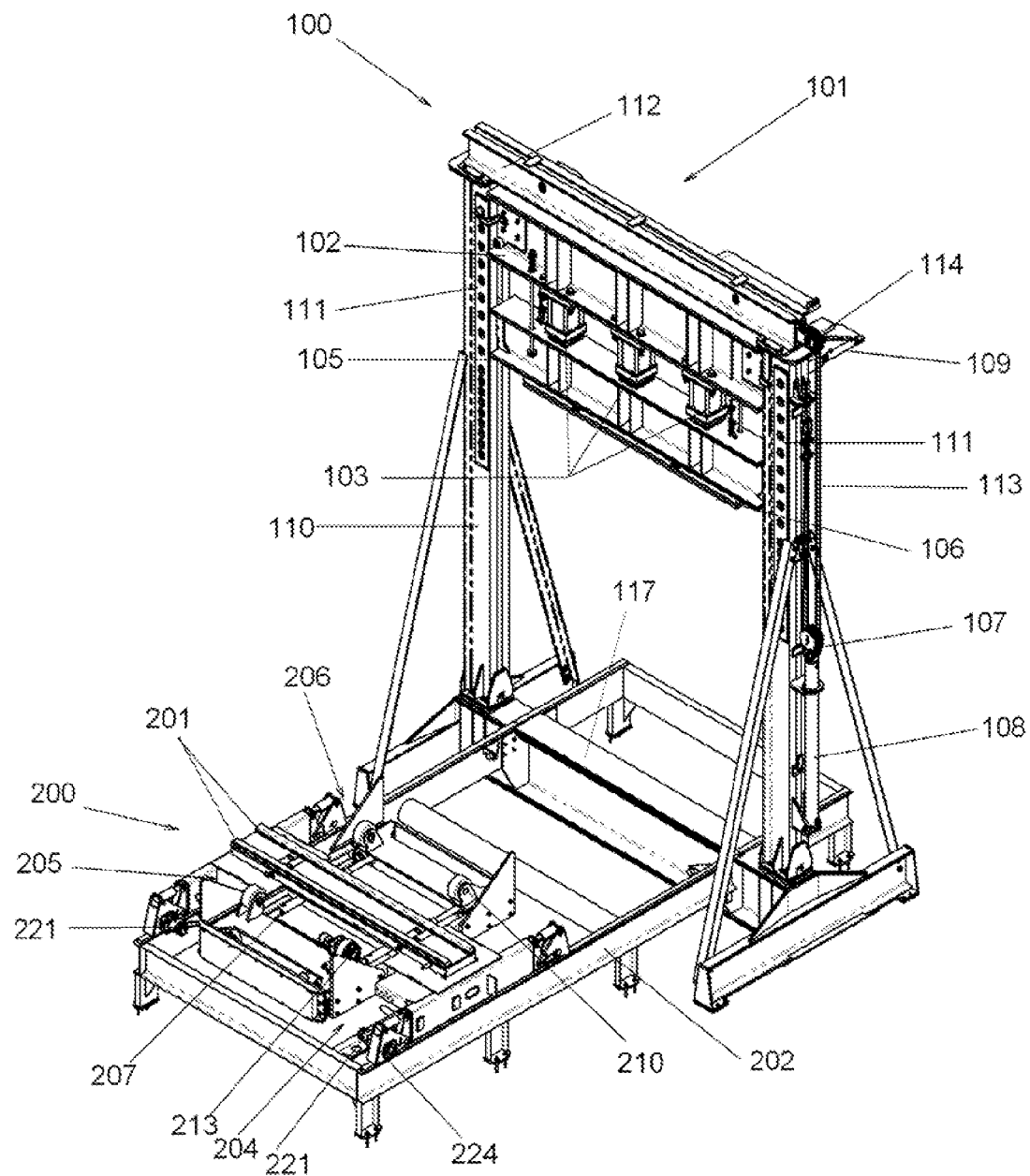
FIG. 1 is a perspective view of an apparatus for positioning a specimen underneath an external load applicator.
Figure 2:
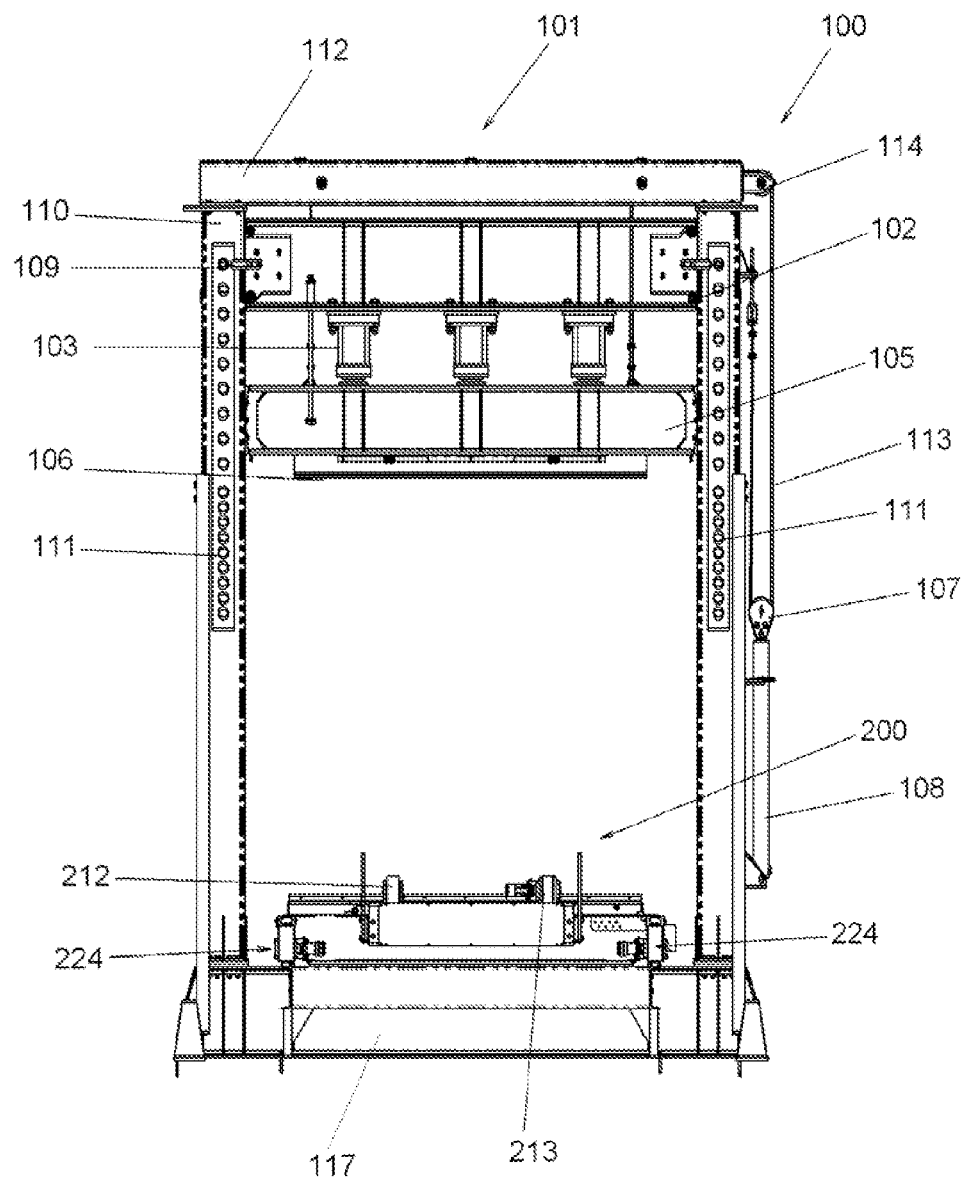
FIG. 2 is a front view of the apparatus shown in FIG. 1.
Figure 3:
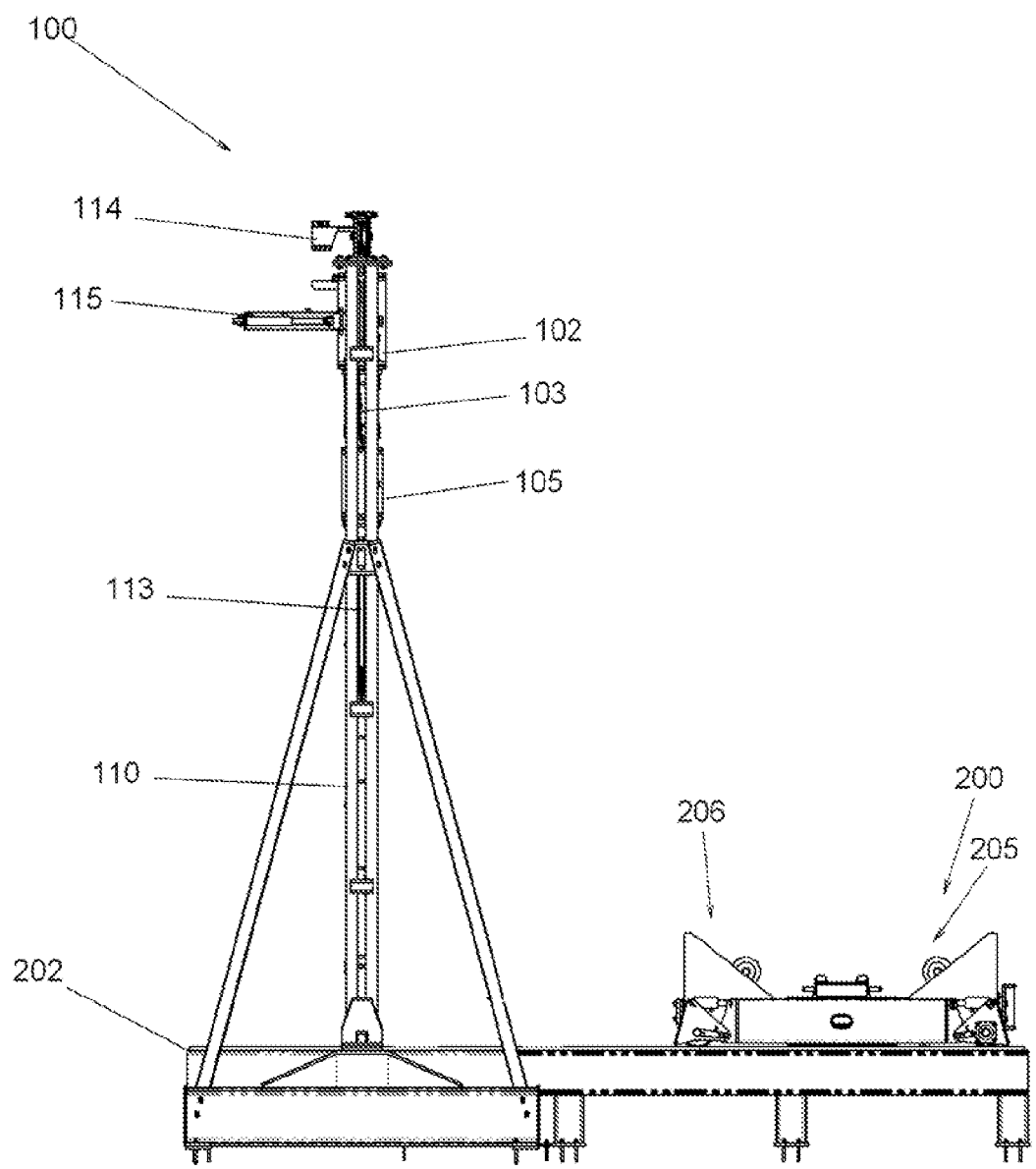
FIG. 3 is a side view of the apparatus shown in FIG. 1.
Figure 4:
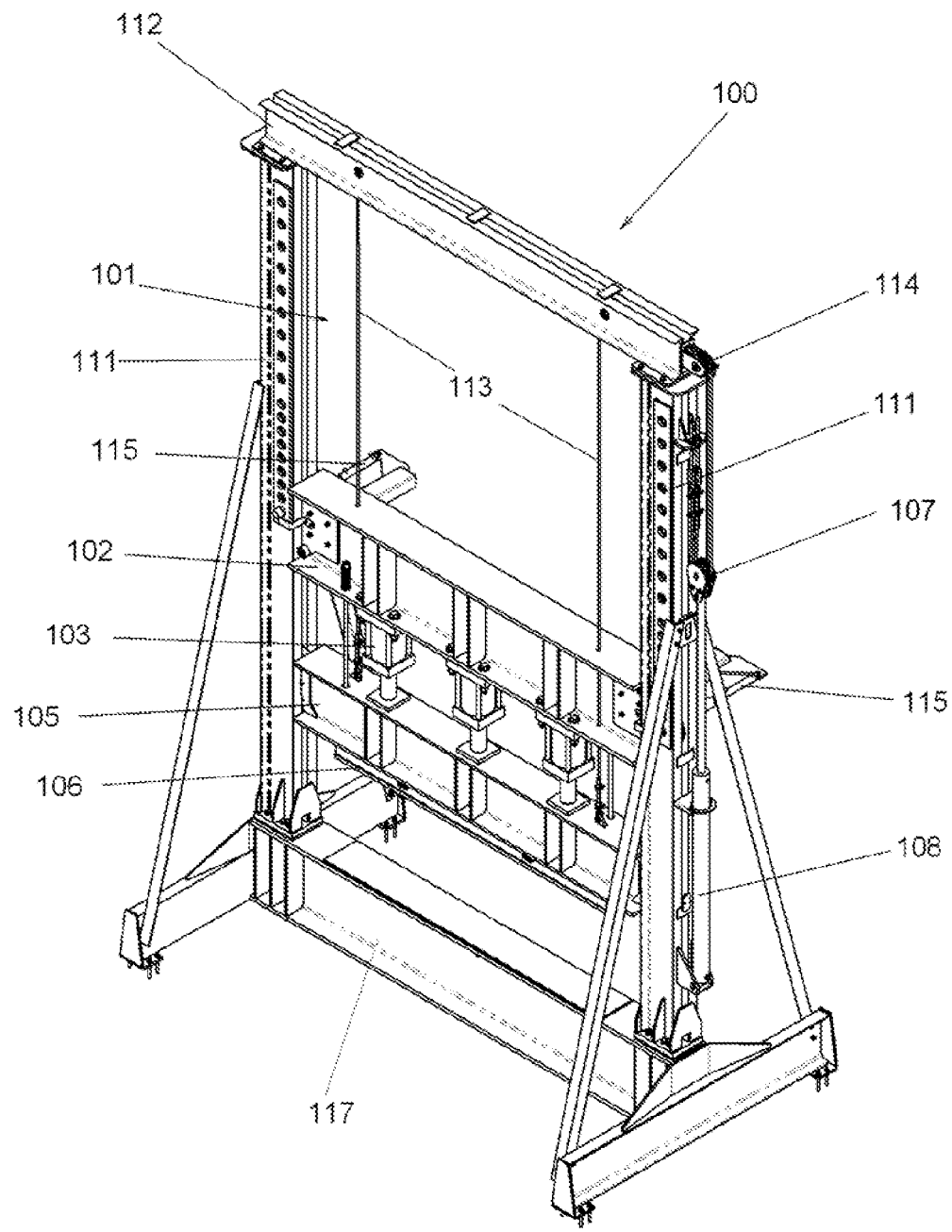
FIG. 4 is a perspective view of the external load applicator of FIG. 1 with the load applicator in a lowered position.
Figure 5:
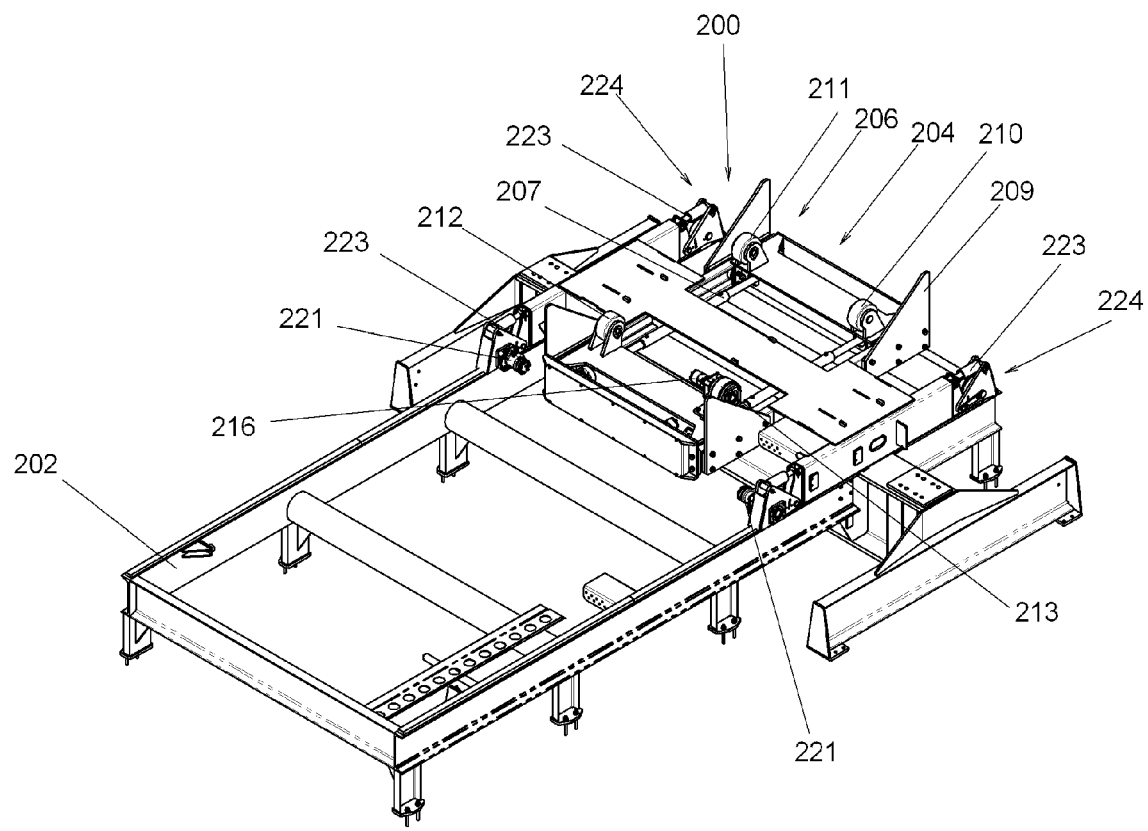
FIG. 5 is a perspective view of the carriage and the defined path for position the specimen underneath the external load applicator.
Figure 6:
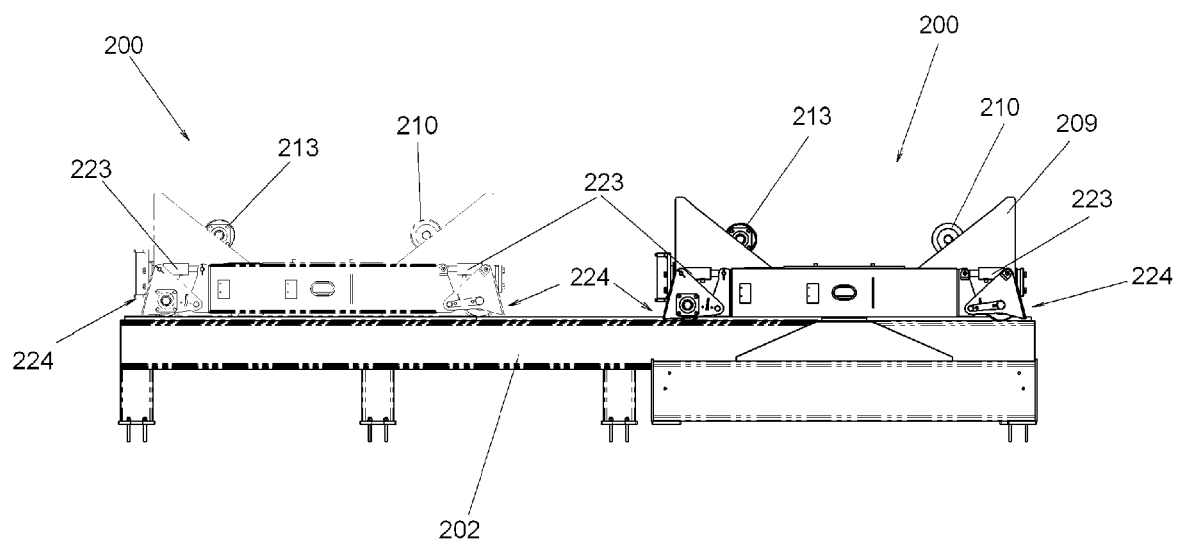
FIG. 6 is a side view of the carriage in two positions on the defined path for transporting the specimen along the defined path.

The drawings illustrate a preferred embodiment of an apparatus 1 for positioning a specimen (not shown) underneath an external load applicator, indicated generally by the reference numeral 100, for the purpose of conducting an "External Load Crushing Test by the Three-Edge Bearing Test Method," in accordance with the testing procedure required by ASTM C 497 (the "Crush Test"). The Crush Test incorporates a three-edge bearing method of loading where an upper bearing 106 presses down upon a specimen to be tested positioned on a pair of lower bearings 201. In this method, it is required to have the specimen's center of gravity centered as near as possible between lower bearings 201 and in-line with upper bearing 106 through which the load is applied. With the specimen's center of gravity positioned between lower bearings 201, the weight of specimen and the force applied through upper bearing 106 is equally dispersed through lower bearings 201. Upper bearing 106 is a rigid wood beam with or without an attached hard rubber strip. Lower bearings 201 are constructed of wood or hard rubber strips and fastened to a wooden or steel beam or directly to a concrete base. The rigidity of lower bearings 201 when fastened the beam or base should not deflect greater than $1/720$ of the specimen length when the maximum load is applied.

External load applicator 100 is comprised of one or more hydraulic rams 103 combined with a positioning beam 102 and a upper load beam 105. Upper load beam 105 has an upper bearing 106 affixed to its underside. Upper bearing 106 engages and crushes the specimen to be tested, via the force applied by hydraulic rams 103.

In the illustrated embodiment, hydraulic rams 103 are disposed between positioning beam 102 and upper load beam 105. Positioning beam 102 and upper load beam 105 are positioned within a vertically standing frame 101, comprised of two vertically extending, spaced-apart parallel beams 110 joined at the top by upper beam 112 and at the bottom by a lower load beam 117, which frame 101 provides a linear path for positioning beam 102 and upper load beam 105.

Positioning beam 102 is selectively positionable to accommodate the diameter of the specimen to be tested. A plurality of spaced-apart holes 111 extend along the length of each of the two vertically parallel beams 110. A pair of hydraulically actuated pins 109 are movable by hydraulic actuators 15 which are affixed to positioning beam 102, in order to engage in selected ones of holes 111 to hold positioning beam 102 in a selected fixed position.

In the preferred embodiment, positioning beam 102 is suspended from cables 113 which pass over pulley 114 affixed to the outer end of upper beam 112. The cables 113 then pass through pulley 107 and are affixed to the beam 110. Pulley 107 is combined with an actuator 108 that is remotely controlled. In this embodiment, hydraulically activated pins 109 are also controlled remotely. When hydraulically activated pins 109 are disengaged from holes 111, positioning beam 102 is held in position by cable 113 and pulley 107. Actuator 108 raises or lowers positioning beam 102 to a predetermined position by moving pulley 107 up or down. When positioning beam 102 reaches the desired position, actuator 108 will move pins 109 to engage holes 111 to fix positioning beam 102 with frame 101.

Lower load beam 117 is positioned in frame 101 directly beneath upper load beam 105. Lower load beam 117 meets the Crush Test specifications by providing a rigid steel beam with a deflection not greater than $1/720$ of the specimen length when the maximum load is applied.

A carriage 200 is provided to support the specimen and transport the specimen along a defined path 202 that extends from a loading position away from frame 101 to an engagement position beneath frame 101 and above lower load beam 117. In the loading position, carriage 200 is positioned such that an operator can load the specimen to be tested on carriage 200 by any suitable means, such as a fork lift. Once the specimen is loaded, carriage 200 transports the specimen to frame 101 along defined path 202 to a position above lower load beam 117. Carriage 200 lowers so that it is contiguous with lower load beam 117.

The carriage will now be discussed more specifically in reference to FIGS. 5-8. When the operator loads the specimen onto carriage 200, it is placed on a load positioning assembly 204, in order to center the specimen on lower bearings 201. Load positioning assembly 204, includes first and second moveable supports 205 & 206, respectively. First and second moveable supports 205 & 206 are combined with one or more actuators 207 adapted for synchronized inward and outward movement with respect to carriage 200. In the illustrative embodiment, actuator 207 is a lead screw 207. First and second moveable supports 205 &206 each have a pair of centering rollers 210, 211, 212, and 213. Centering rollers 210, 211, 212, and 213 are of sufficient quality and strength to support the specimen which may weigh several tons. Optionally, safety members 209 are combined with first and second moveable supports 205 & 206 and positioned behind centering rollers 210, 211, 212, and 213 to prevent the specimen from rolling off carriage 200.

To load a specimen, the operator positions the specimen on centering rollers 210, 211, 212, and 213. The specimen is supported above carriage 200 to allow the operator to position lower bearings 201 underneath the specimen in accordance with the requirements of the Crush Test. Since the specimen is supported directly above carriage 200, the operator can easily center bearings 201 underneath the specimen.

Specimens are unlikely to be perfectly round and often they are oval-shaped. As stated above, its desired to have the specimen's center of gravity between lower bearings 201 so that the specimen's weight is equally dispersed. The specimen is rotatably supported on centering rollers 210, 211, 212, and 213, which allow the specimen to rotate so that its center of gravity can be centered above the mid point between lower bearings 201. In an embodiment, one of the centering rollers 210, 211, 212, and 213 is driven with a drive mechanism 216. Drive mechanism 216 turns one of rollers 210, 211, 212, and 213 which causes specimen to rotate. The operator can automatically rotate the specimen until its center of gravity is positioned directly over and in between lower bearings 201.

When the specimen is centered above lower bearings 201, first and second moveable supports 205 &206 are driven outward away from each other to lower the specimen on to lower bearings 201. As previously stated, the specimen is positioned on rollers 210, 211, 212, and 213. As opposing rollers 210, 211 and 212, 213 are driven outward and away from each other the specimen moves downward until it rests on lower bearings 201. With the specimen on lower bearings 201 it is ready for transport along defined path 202 to the engagement position underneath upper bearing 106.

Figure 7:
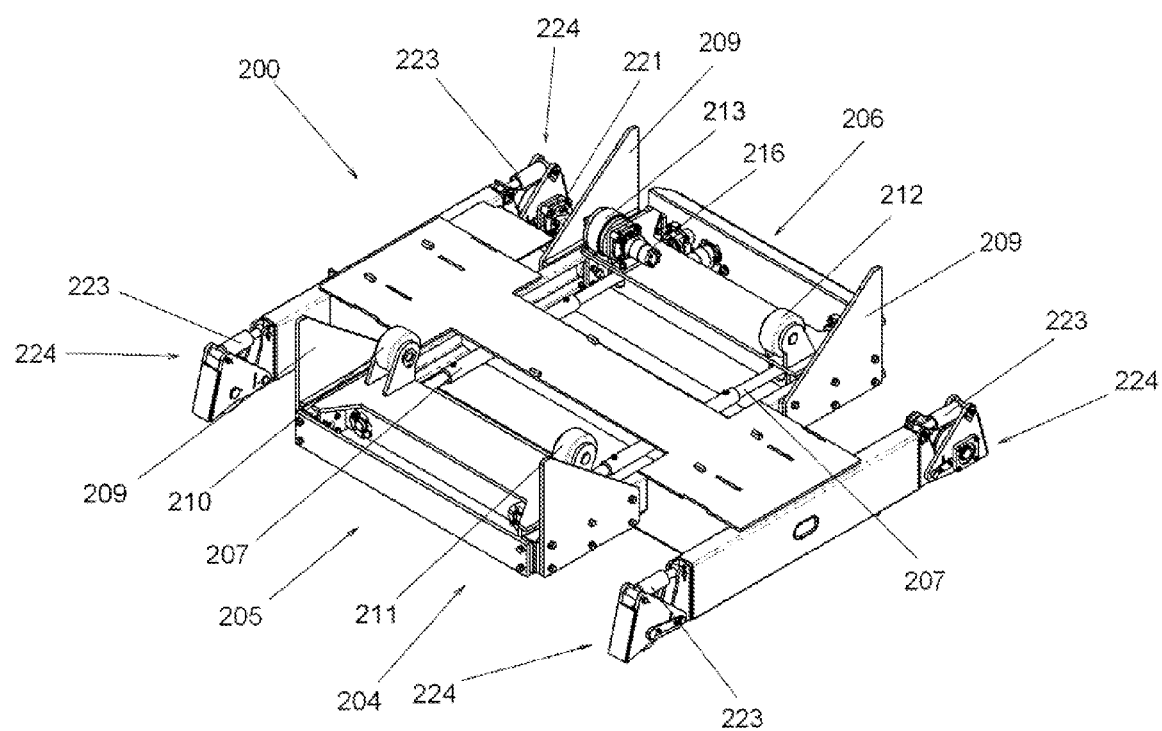
FIG. 7 is a perspective view of the carriage shown in FIG. 6.
Figure 8:
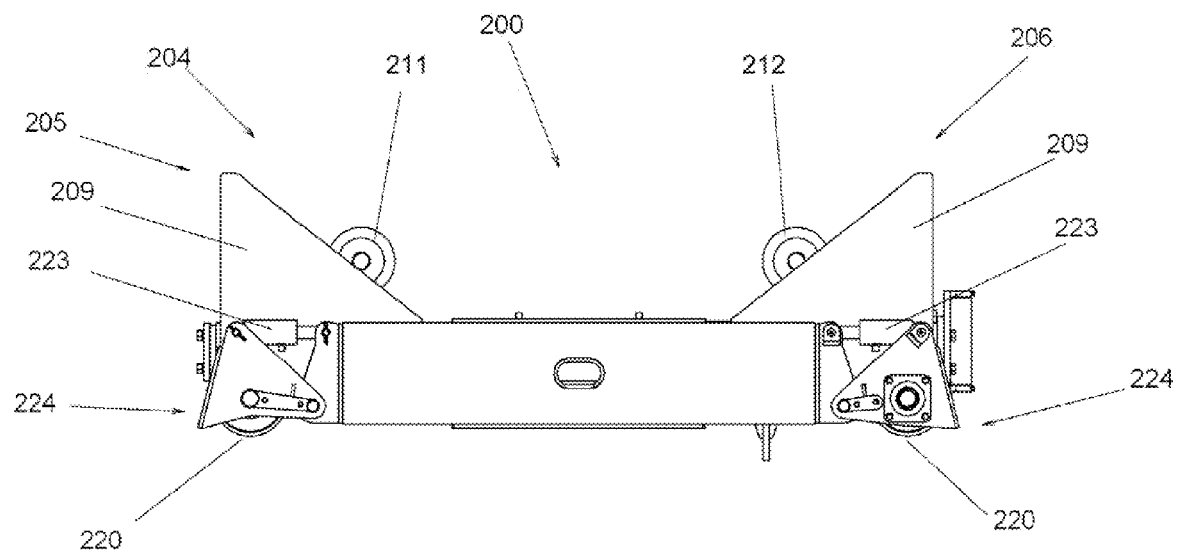
FIG. 8 is a side view of the carriage shown in FIG. 7.
Figure 9:
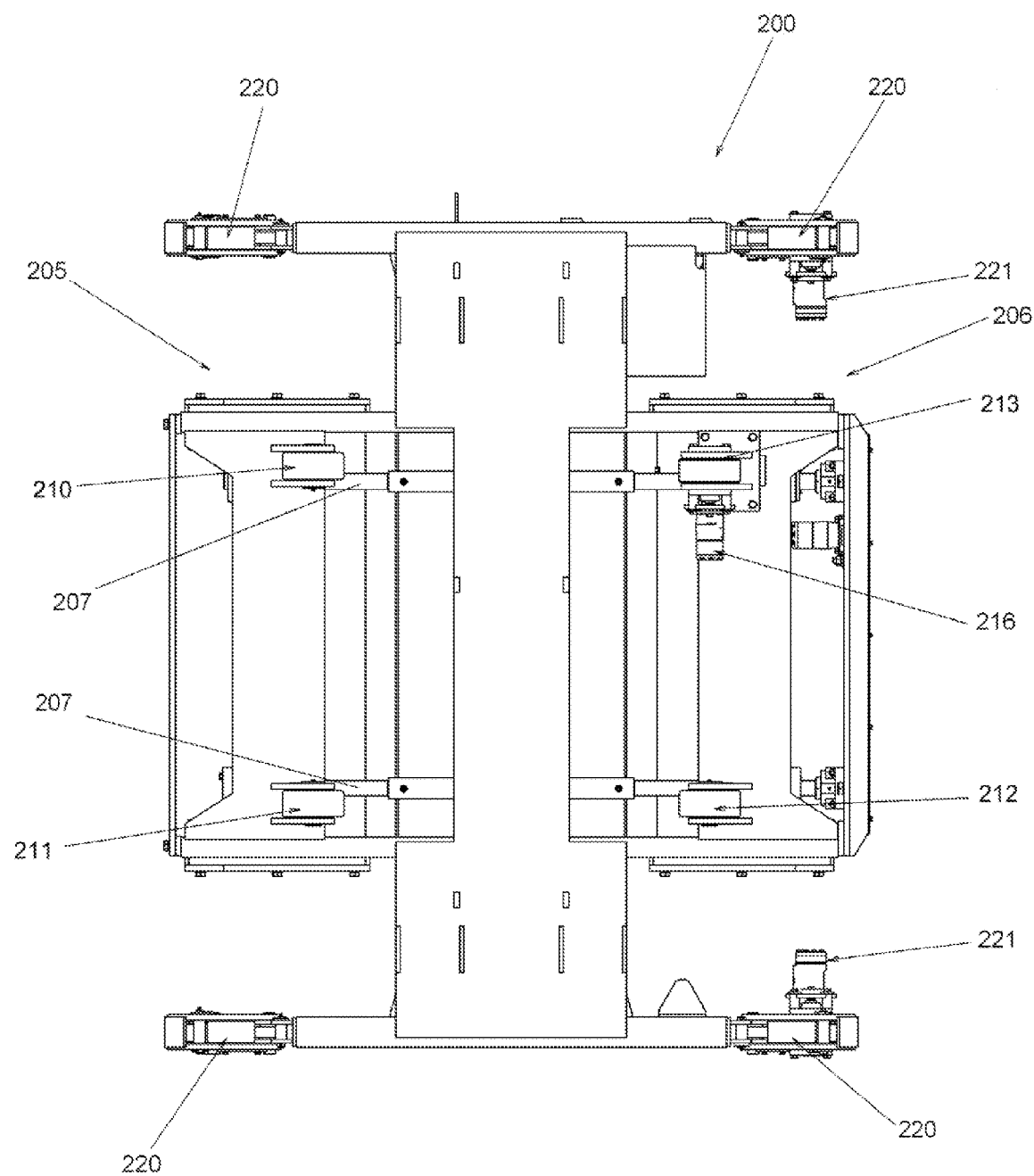
FIG. 9 is a top view of the carriage shown in FIG. 6.
Figure 10:
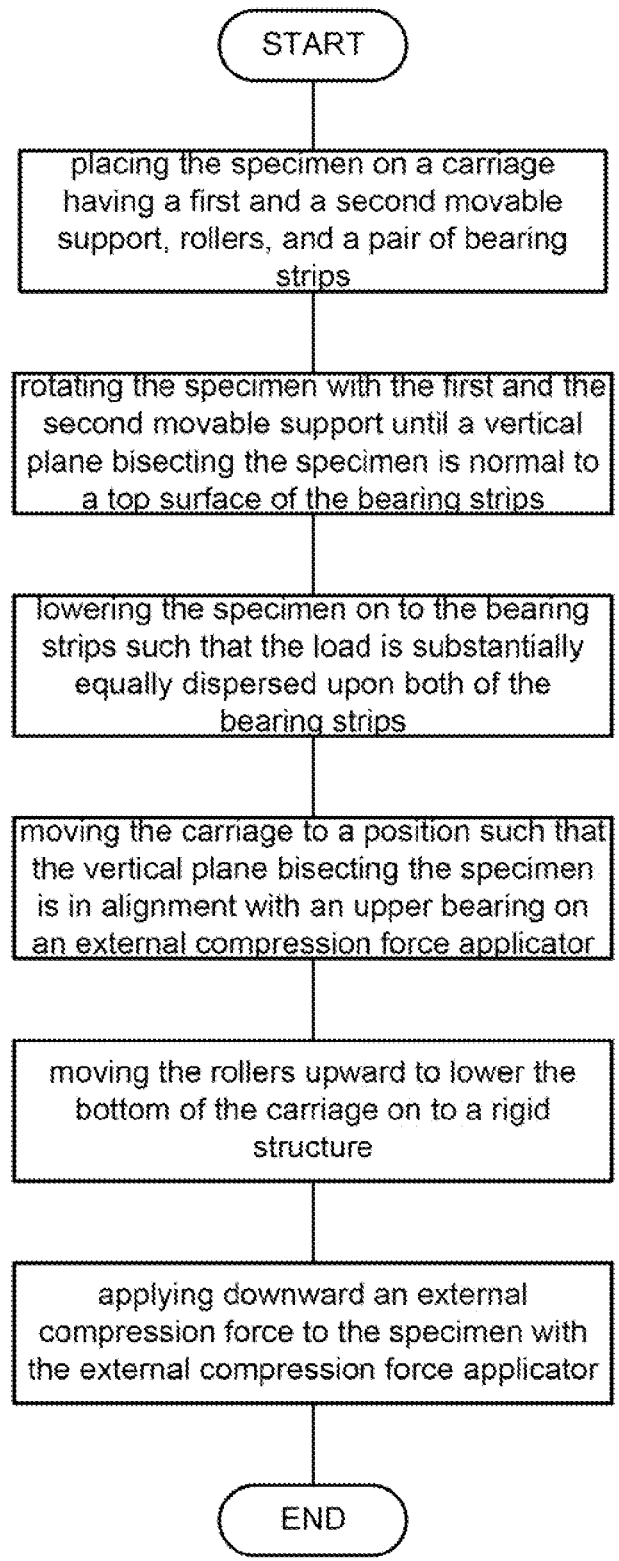
FIG. 10 is a flow chart for a method for positioning a specimen for destructive testing.

Carriage 200 is supported on four rollers 220 positioned at each corner of carriage 200. Referring to FIGS. 7 & 9, two rollers 220 are combined with one or more motors 221 to remotely move carriage 200 along defined path 202. Rollers 220 pivot between a position engaged with defined path 202 and a position disengaged from defined path 202 by extending and retracting cylinder 223. Rollers 220 are enclosed by a substantially triangular shaped pivot assembly 224. Cylinder 223 is combined between the apex of pivot assembly 224 and carriage 200 and pivots about a pivot point 225. Each of cylinders 223 are remotely controllable to uniformly raise and lower carriage 200.

When carriage 200 arrives at the engagement position with the specimen underneath upper bearing 106 and above lower load beam 117, rollers 220 are pivoted upwardly to engage carriage 200 contiguous with lower load beam 117 of external load applicator 100, such that upper bearing 106 can engage the specimen and carriage 200 remains stationary.

Although the drawings have illustrated carriage 200 that moves along defined path 202, similar principles apply to a stationary carriage 200 with a moveable frame 101 along a defined path 202. Moreover, the principles are applicable to a method for positioning a specimen for destructive testing. The method begins by placing the specimen on centering rollers 210-213 of carriage 200 and positioning lower bearing 201 underneath the specimen. The specimen is then rotated until a vertical plane bisecting the specimen is normal to a top surface of lower bearings 201. Once the specimen is centered, it is lowered on to lower bearings 201, such that the weight is substantially equally dispersed upon both of lower bearings 201. The specimen is then positioned with respect to upper bearing 106, such that the vertical plane bisecting the specimen is in alignment with upper bearing 106. When the specimen is aligned with lower bearings 201, a first and second moveable support 205 & 206, respectively are moved outward to lower the specimen on to carriage 200. Rollers 220, that support the carriage 200, are pivoted upward to lower the carriage to a stationary position. Finally, external force is applied to the specimen through upper bearing 106.

Having thus provided a disclosure in connection with the preferred embodiments thereof, it will be evident to those skilled in the art that various revisions can be made to the preferred embodiments described herein without departing from the spirit and scope of this disclosure. It is my intention, however, that all such revisions and modifications that are evident to those skilled in the art will be included within the scope of the following claims.

What is claimed is:

1. An apparatus for positioning a specimen relative to an external force applicator for the purpose of applying an external compression force to the specimen for test purposes, the apparatus for positioning the specimen comprising:
   a defined path extending between a loading position away from the external force applicator and an engagement position where the external compression force can be applied to the specimen by the external force applicator;
   a carriage adapted to support the specimen, the carriage being positioned on the defined path for movement relative to the external force applicator between a loading position away from the external force applicator and an engagement position where the external force applicator can engage the specimen to conduct the test;
   a load positioning assembly combined with the carriage to position the test piece on the carriage, wherein the load positioning assembly further comprises a first and a second moveable support adapted for synchronized longitudinal inward and outward movement with respect to the center of the carriage.

2. The apparatus for positioning the specimen of claim 1, and further comprising at least two rollers on opposite lateral sides of the carriage for selectively supporting the carriage for movement along the path, wherein the rollers are moveable between a first position wherein the carriage is supported above the path for movement along the path and a second position wherein the carriage is contiguous with a rigid base such that the external force applicator can engage the specimen and the carriage remains stationary.

3. The apparatus for positioning the specimen of claim 2, and further comprising an actuator combined with the rollers to move the rollers between the first position wherein the carriage is supported above the path for movement along the path and the second position wherein the carriage is contiguous with the path such that the external force applicator can engage the specimen and the carriage remains stationary.

4. The apparatus for positioning the specimen of claim 1, and further comprising a pair of parallel bearings rectangular in cross section, wherein the specimen is supported above the carriage by the first and second moveable support such that the pair of parallel bearings are positionable laterally across the carriage and under the specimen so that the weight of the specimen is substantially centered between the pair of parallel bearings when the specimen is lowered on to the pair of parallel bearings when the first and second moveable supports move outward with respect to the center of the carriage.

5. The apparatus for positioning the specimen of claim 4, wherein the first and second moveable support each further comprise a centering roller for rotationally supporting the specimen so that the specimen is moveable to a center position with its center of gravity between the pair of parallel bearings.

6. The apparatus for positioning the specimen of claim 5, and further comprising a drive mechanism combined with one of the centering rollers to center the specimen remotely.

7. The apparatus for positioning the specimen of claim 1, and further comprising at least two rollers combined to the carriage and positioned on opposite lateral sides of the carriage for selectively supporting the carriage for movement along the path, wherein the rollers are moveable with respect to the carriage between a first position wherein the carriage is supported above the path for movement along the path and a second position wherein the carriage is contiguous with the path such that the external force applicator can engage the specimen and the carriage remains stationary.

8. An apparatus for positioning a specimen relative to an external force applicator for the purpose of applying an external compression force to the specimen for test purposes, the apparatus for positioning the specimen comprising:
   a defined path extending between a loading position away from the external force applicator and an engagement position where the external compression force can be applied to the specimen by the external force applicator;
   a carriage adapted to support the specimen, the carriage being positioned on the defined path for movement relative to the external force applicator between a loading position away from the external force applicator and an engagement position where the external force applicator can engage the specimen to conduct the test;
   at least two rollers combined to the carriage and positioned on opposite lateral sides of the carriage for selectively supporting the carriage for movement along the path, wherein the rollers are moveable with respect to the carriage between a first position wherein the carriage is supported above the path for movement along the path and a second position wherein the carriage is contiguous with the path such that the external force applicator can engage the specimen and the carriage remains stationary; and
   an actuator combined with the rollers to move the rollers between the first position wherein the carriage is supported above the path for movement along the path and the second position wherein the carriage is contiguous with the path such that the external force applicator can engage the specimen and the carriage remains stationary.

9. The apparatus for positioning the specimen of claim 8, and further comprising at least two rollers on opposite lateral sides of the carriage for selectively supporting the carriage for movement along the path, wherein the rollers are moveable between a first position wherein the carriage is supported above the path for movement along the path and a second position wherein the carriage is contiguous with the path such that the external force applicator can engage the specimen and the carriage remains stationary.

10. The apparatus for positioning the specimen of claim 9, and further comprising an actuator combined with the rollers to move the rollers between the first position wherein the carriage is supported above the path for movement along the path and the second position wherein the carriage is contiguous with a rigid base such that the external force applicator can engage the specimen and the carriage remains stationary.

11. The apparatus for positioning the specimen of claim 10, and further comprising a load positioning assembly combined with the carriage to position the test piece on the carriage.

12. The apparatus for positioning the specimen of claim 11, wherein the load positioning assembly further comprises a first and a second moveable support adapted for synchronized longitudinal inward and outward movement with respect to the center of the carriage.

13. The apparatus for positioning the specimen of claim 12, and further comprising a pair of parallel bearings rectangular in cross section, wherein the specimen is supported above the carriage by the first and second moveable support such that the pair of parallel bearings are positionable laterally across the carriage and under the specimen so that the weight of the specimen is substantially centered between the pair of parallel bearings when the specimen is lowered on to the pair of parallel bearings when the first and second moveable supports move outward with respect to the center of the carriage.

14. The apparatus for positioning the specimen of claim 13, wherein the first and second moveable support each further comprise a centering roller for rotationally supporting the specimen so that the specimen is moveable to a center position with its center of gravity between the pair of parallel bearings.

15. The apparatus for positioning the specimen of claim 14, and further comprising a drive mechanism combined with one of the centering rollers to center the specimen remotely.

16. A method for positioning a specimen for destructive testing, the method comprising:
    placing the specimen on a carriage having a first and a second movable support, rollers, and a pair of bearing strips;
    rotating the specimen with the first and the second movable support until a vertical plane bisecting the specimen is normal to a top surface of the bearing strips;
    lowering the specimen on to the bearing strips such that the load is substantially equally dispersed upon both of the bearing strips;
    moving the carriage to a position such that the vertical plane bisecting the specimen is in alignment with an upper bearing on an external compression force applicator;
    moving the rollers upward to lower the bottom of the carriage on to a rigid structure; and
    applying downward an external compression force to the specimen with the external compression force applicator.

17. The method of claim 16, wherein the moving motion of the rollers is a pivoting motion.

18. The method of claim 17, wherein the step of lowering the specimen on to the bearing strips further comprises moving the first and the second moveable support linearly outward to lower the specimen.

19. An apparatus for positioning a specimen relative to an external compression force applicator for engaging the specimen for test purposes, the apparatus comprising:
    an external compression force applicator;
    a defined path extending between a first position away from the external compression force applicator and a second position underneath the external compression force applicator; and
    a carriage adapted to support the specimen, the carriage being positioned on the defined path for movement relative to the external compression force applicator between the first position which is a loading position away from the external compression force applicator and the second position which is an engagement position where the external compression force applicator can compress the specimen to conduct the test; and
    a load positioning assembly combined with the carriage to position the test piece on the carriage, wherein the load positioning assembly further comprises a first and a second moveable support adapted for synchronized longitudinal inward and outward movement with respect to the center of the carriage.

20. The apparatus of claim 19, and further comprising at least two rollers on opposite lateral sides of the carriage for selectively supporting the carriage for movement along the defined path, wherein the rollers are moveable between a first position wherein the carriage is supported above the path for movement along the path and a second position wherein the carriage is contiguous with the path such that the external force applicator can engage the specimen and the carriage remains stationary.

21. The apparatus of claim 20, and further comprising an actuator combined with the rollers to move the rollers between the first position wherein the carriage is supported above the path for movement along the path and the second position wherein the carriage is contiguous with a rigid base such that the external force applicator can engage the specimen and the carriage remains stationary.

22. The apparatus of claim 19, and further comprising a pair of parallel bearings rectangular in cross section, wherein the specimen is supported above the carriage by the first and second moveable support such that the pair of parallel bearings are positionable laterally across the carriage and under the specimen so that the weight of the specimen is substantially centered between the pair of parallel bearings when the specimen is lowered on to the pair of parallel bearings when the first and second moveable supports move outward with respect to the center of the carriage.

23. The apparatus of claim 22, wherein the first and second moveable support each further comprise a centering roller for rotationally supporting the specimen so that the specimen is moveable to a center position with its center of gravity between the pair of parallel bearings.

24. The apparatus of claim 23, and further comprising a drive mechanism combined with one of the centering rollers to center the specimen remotely.

25. An apparatus for positioning a specimen relative to an external force applicator for the purpose of applying an external force to the specimen for test purposes, the apparatus for positioning the specimen comprising:
    a defined path extending between a loading position away from the external force applicator and an engagement position where the external force can be applied to the specimen by the external force applicator;
    a carriage adapted to support the specimen, the carriage being positioned on the defined path for movement relative to the external force applicator between a loading position away from the external force applicator and an engagement position where the external force applicator can engage the specimen to conduct the test; and
    a load positioning assembly combined with the carriage to position the test piece on the carriage;
    a first and a second moveable support adapted for synchronized longitudinal inward and outward movement with respect to the center of the carriage; and a pair of parallel bearings rectangular in cross section, wherein the specimen is supported above the carriage by the first and second moveable support such that the pair of parallel bearings are positionable laterally across the carriage and under the specimen so that the weight of the specimen is substantially centered between the pair of parallel bearings when the specimen is lowered on to the pair of parallel bearings when the first and second moveable supports move outward with respect to the center of the carriage.

26. The apparatus for positioning the specimen of claim 25, wherein the first and second moveable support each further comprise a centering roller for rotationally supporting the specimen so that the specimen is moveable to a center position with its center of gravity between the pair of parallel bearings.

27. The apparatus for positioning the specimen of claim 26, and further comprising a drive mechanism combined with one of the centering rollers to center the specimen remotely.

\* \* \* \* \*